US009193599B2

(12) United States Patent
Odén et al.

(10) Patent No.: US 9,193,599 B2
(45) Date of Patent: Nov. 24, 2015

(54) MANUFACTURE OF STRUCTURES COMPRISING SILICON DIOXIDE ON A SURFACE

(75) Inventors: Magnus Odén, Tullinge (SE); Emma Björk, Linköping (SE)

(73) Assignee: Nanolith Sverige AB (SE)

( * ) Notice: Subject to any disclaimer, the term of this patent is extended or adjusted under 35 U.S.C. 154(b) by 234 days.

(21) Appl. No.: 13/825,472

(22) PCT Filed: Sep. 21, 2011

(86) PCT No.: PCT/EP2011/066384
§ 371 (c)(1),
(2), (4) Date: May 31, 2013

(87) PCT Pub. No.: WO2012/038457
PCT Pub. Date: Mar. 29, 2012

(65) Prior Publication Data
US 2014/0004306 A1 Jan. 2, 2014

Related U.S. Application Data

(60) Provisional application No. 61/385,693, filed on Sep. 23, 2010.

(30) Foreign Application Priority Data

Sep. 23, 2010 (SE) ...................................... 1050988

(51) Int. Cl.
*C01B 33/12* (2006.01)
*C01B 37/02* (2006.01)
*B82Y 30/00* (2011.01)
*B82Y 40/00* (2011.01)
*C01B 33/187* (2006.01)
*B32B 3/26* (2006.01)
*B44C 1/22* (2006.01)
*A61K 47/02* (2006.01)
*C01B 33/18* (2006.01)
*C01B 33/193* (2006.01)

(52) U.S. Cl.
CPC ................ *C01B 37/02* (2013.01); *A61K 47/02* (2013.01); *B32B 3/263* (2013.01); *B44C 1/227* (2013.01); *B82Y 30/00* (2013.01); *B82Y 40/00* (2013.01); *C01B 33/187* (2013.01); *C01B 33/18* (2013.01); *C01B 33/193* (2013.01); *C01P 2002/01* (2013.01); *C01P 2004/03* (2013.01); *C01P 2004/04* (2013.01); *C01P 2004/13* (2013.01); *C01P 2004/64* (2013.01); *C01P 2006/16* (2013.01); *Y10T 428/24479* (2015.01)

(58) Field of Classification Search
CPC ...... C01B 33/18; C01B 33/187; C01B 33/193
USPC ......................................... 423/335, 338, 339
See application file for complete search history.

(56) References Cited

U.S. PATENT DOCUMENTS

| 4,973,563 | A | * | 11/1990 | Prigge et al. ................... 438/692 |
| 2002/0041932 | A1 | | 4/2002 | Ogawa |
| 2003/0012931 | A1 | | 1/2003 | Kuroda et al. |
| 2012/0192762 | A1 | | 8/2012 | Yabe et al. |

OTHER PUBLICATIONS

Zhao, Continuous mesoporous silica films with highly ordered large pore structures, 1998, Advanced Materials, 10, 1380-1385.*
Bai et al.; Gold Nanoparticles-Mesoporous Silica Composite Used as an Enzyme Immobilization Matrix for Amperometric Glucose Biosensor Construction, Sensors and Actuators B: Chemical: International Journal Devoted to Research and Development of Physical and Chemical Transducers, Elsevier SA, Switzerland, May 16, 2007, 124:1, pp. 179-186, XP022080520.
De Witte, K. et al.; Multi-Step Loading of Titania on Mesoporous Silica: Influence of the Morphology and the Porosity on the Catalytic Degradation of Aqueous Pollutants and VOCs, Applied Catalysis B: Environmental, Elsevier, Oct. 25, 2008, 84:1-2, pp. 125-132, XP025435054.
Hu et al.; Large-Area Silica Nanotubes With Controllable Geometry on Silicon Substrates, Applied Surface Science, Elsevier, Amsterdam. NL, Jan. 1, 2009 255:6, pp. 3563-3566. XP025865643.
International Search Report and Written Opinion for Application No. PCT/EP2011/066381 dated Mar. 26, 2013.
International Search Report and Wrtitten Opinion for Application No. PCT/EP2011/066384 dated Mar. 26, 2013.
Johansson, E.M. et al: Synthesis and Characterization of Large Mesoporous Silica SBA-15 Sheets with Ordered Accessible 18 nm Pores, Materials Letters, North Holland Publishing Company, Amsterdam, NL, Oct. 15, 2009, 63:24-25, pp. 2129-2131, XP026467350.
Johansson, Emma M. et al.; The Effects on Pore Size and Particle Morphology of Heptane Additions to the Synthesis of Mesoporous Silica SBA-15, Microporous and Mesoporous Materials, Sep. 1, 2010,133:1-3, pp. 66-74, XP055014159.
Mesa M. et al.; Morphology and Porosity Characteristics Control of SBA-16 Mesoporous Silica. Effect of the Triblock Surfactant Pluronic F127 Degradation During the Synthesis. Solid State Sciences, Elsevier, Paris. FR, Aug. 1, 2005, 7:8, pp. 990-997, XP004997002.

(Continued)

*Primary Examiner* — Matthew E Hoban
*Assistant Examiner* — James Fiorito
(74) *Attorney, Agent, or Firm* — Lerner, David, Littenberg, Krumholz & Mentlik, LLP

(57) ABSTRACT

A substrate surface comprises at least partially at least one elongated structure, wherein each elongated structure comprises a plurality of channels, said channels extending in the direction of the longitudinal axis of the elongated structure, wherein said at least one elongated structure comprises silicon dioxide. The structures are manufactured by: a) providing a reaction solution comprising a silicate, a micelle forming agent, an alkane, a salt, and at least 1.5 M HCl, having a pH of 2 or lower, b) stirring not more than 10 minutes, c) bringing the reaction solution into contact with a substrate surface and d) treating the obtained material with one method selected from a) heat treating the material above 300° C., b) treating the material with at least one selected from $H_2O_2$, and $H_2SO_4$, c) treating the material with microwaves to digest the micelle forming agent.

8 Claims, 7 Drawing Sheets

(56) References Cited

OTHER PUBLICATIONS

Shiori Kubo et al.; Salt-Induced Formation of Uniform Fiberlike SBA-15 Mesoporous Silica Particles and Application to Toluene Adsorption, Langmuir, Nov. 1, 2007, 23:23, pp. 11761-11768, XP55014158.

Wang Y et al.; Synthesis of Length Controllable Mesoporous SBA-15 Rods, Materials Chemistry and Physics, Elsevier SA. Switzerland, Taiwan, Republic of China, Jun. 15, 2009, 115:2-3, pp. 649-655. XP026018602.

Zhao, D. et al.; High-Yield Synthesis of Periodic Mesoporous Silica Rods and Their Replication to Mesoporous Carbon Rods, Advanced Materials, Wiley VCH Verlag. DE, Dec. 3, 2002, 14:23, pp. 1742-1745, XP002418214.

U.S. Office Action for U.S. Appl. No. 13/825,454 dated Jan. 7, 2015.

\* cited by examiner

MANUFACTURE OF STRUCTURES COMPRISING SILICON DIOXIDE ON A SURFACE

CROSS-REFERENCE TO RELATED APPLICATIONS

The present application is a national phase entry under 35 U.S.C. §371 of International Application No. PCT/EP2011/066384 filed Sep. 21, 2011, published in English, which claims priority from U.S. Application No. 61/385,693 filed Sep. 23, 2010, and Swedish Application No. 1050988-3 filed Sep. 23, 2010 all of which are incorporated herein by reference.

TECHNICAL FIELD

The present invention relates generally to a method for the manufacture of structures attached to a surface as well as a surface substrate comprising the structures.

BACKGROUND

Ordered mesoporous silica can be synthesized in a variety of pore sizes, pore shapes and morphologies. Due to its potential applications in e.g. separation, catalysis, adsorption and as a template, this group of materials has received much interest the last decades. Depending on the application various morphologies, pore sizes and pore shapes are preferable.

The pore size of SBA-15 is normally 6-9 nm but it can be increased by e.g. adding swelling agents such as 1,3,5-trimethylbenzene (TMB) or by varying the hydrothermal treatment time and temperature. Increasing the pore size using swelling agent is possible up to a certain limit, but due to a phase transition from ordered hexagonal pores to disordered mesocellular foams this is the maximum pore size obtained. Low temperature syntheses with alkanes and $NH_4F$ can increase the pore size where the morphology can be varied by varying synthesis parameters.

E. Johansson et al in Microporous and Mesoporous Materials, volume 133, issue 1-3, pages 66-74, September 2010 discloses manufacture of mesoporous silica in the form of crystallites with hexagonally arranged pores running through the crystallites. The crystallites are always attached to each other. The crystallites can be attached end-to-end to form fibers, or the crystallites can be attached side-by-side to form sheets. It is disclosed that heptane in the presence of $NH_4F$ works as a pore swelling agent. The HCl concentration was varied between 1.37-1.98 M.

E. Johansson et al in Materials Letters, volume 63, Issue 24, pages 2129-2131, October 2009 discloses mesoporous silica in the form of crystallites attached side-by-side to sheets, where the pores are parallel to the sheet normal.

The mentioned crystallites can be used for a number of different applications, but a problem in the state of art is how to prepare structures which are attached to a surface and which are at least partially perpendicular to the surface.

SUMMARY

It is an object of the present invention to alleviate at least some of the disadvantages of the prior art and to provide structures attached to a surface as well as a method for the manufacture of the structures.

The inventors have performed extensive research and have unexpectedly found a way to obtain useful structures on a surface.

In a first aspect there is provided a substrate surface at least partially comprising at least one elongated structure, wherein each elongated structure comprise a plurality of channels, said channels extending in the direction of the longitudinal axis of the elongated structure, wherein said at least one elongated structure comprises silicon dioxide.

In a second aspect there is provided a method for the manufacture of structures on a surface, said method comprising the steps of:
  providing a reaction solution, said reaction solution comprising a silicate, a micelle forming agent, an alkane, a salt, and at least 1.5 M HCl, said reaction solution having a pH of 2 or lower,
  stirring not more than 10 minutes,
  bringing the reaction solution into contact with a substrate surface
  treating the obtained material to remove said micelle forming agent with one method selected from a) heat treating the material above 300° C., b) treating the material with at least one selected from $H_2O_2$, and $H_2SO_4$, c) treating the material with microwaves to digest the micelle forming agent.

BRIEF DESCRIPTION OF THE DRAWINGS

The invention is described with reference to the following drawings in which.

DETAILED DESCRIPTION

Figure 1:
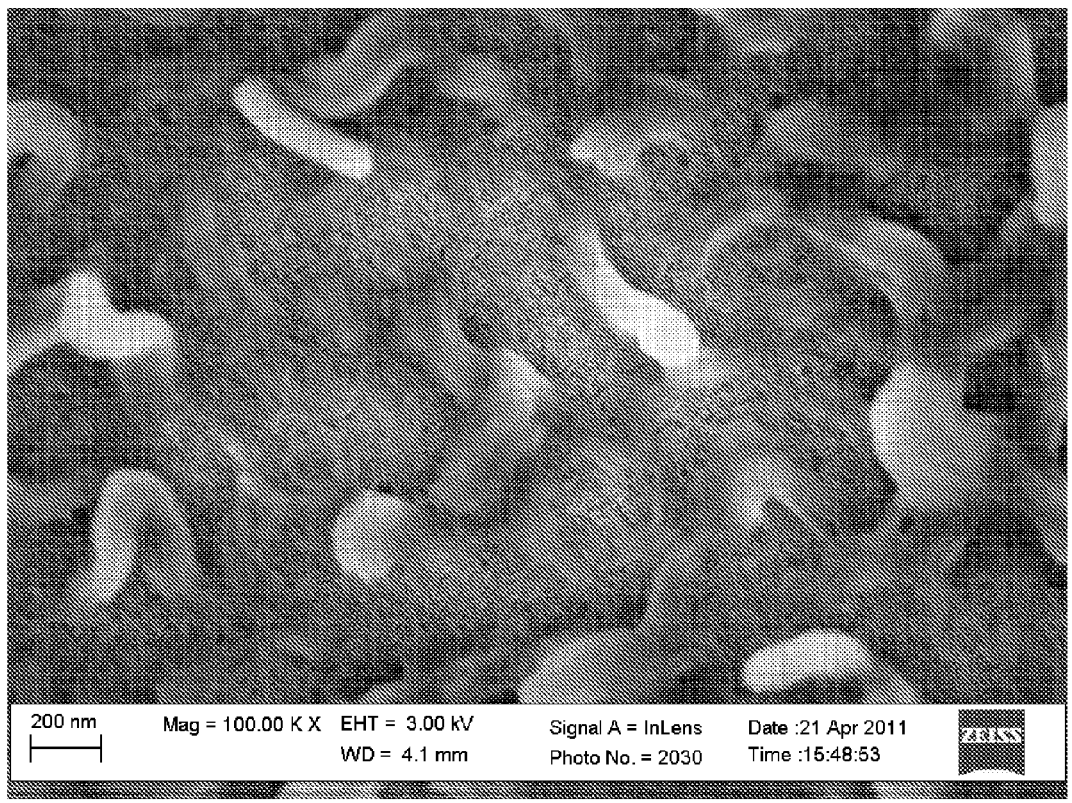
FIG. 1 shows an electron micrograph of structures according to the invention.

Before the invention is disclosed and described in detail, it is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

The term "about" as used in connection with a numerical value throughout the description and the claims denotes an interval of accuracy, familiar and acceptable to a person skilled in the art. Said interval is ±10%.

As used throughout the claims and the description the term mesoporous material denotes a material containing pores with diameters between 2 and 50 nm.

In a first aspect there is provided a substrate surface at least partially comprising at least one elongated structure, wherein each elongated structure comprise a plurality of channels, said channels extending in the direction of the longitudinal axis of the elongated structure, wherein said at least one elongated structure comprises silicon dioxide.

In one embodiment the channels have a diameter from about 6 nm to about 22 nm. In one embodiment the diameter of the channels is from 10 to 20 nm. In another embodiment the diameter of the channels is from 8 to 22 nm. In an alternative embodiment the diameter of the channels is from 12 to 20 nm. In an alternative embodiment the diameter of the channels is from 12 to 18 nm. In another embodiment the diameter of the channels is from 13 to 18 nm. In an alternative embodiment the diameter of the channels is from 13 to 16 nm. In another embodiment the diameter of the channels is about 18 nm. It must be realized that the channels do not necessarily have perfect circular cross sections due to the manufacturing process.

In one embodiment the at least one elongated structure has a diameter from 50 nm to about 800 nm.

Neither the elongated structure nor the channels necessarily have a perfectly circular cross section, and the diameter for non circular structures and channels is defined as the maximum distance between any two points on the circumference of a perpendicular cross section.

In one embodiment the at least one elongated structure has a length from 50 nm to about 1000 nm.

In one embodiment the channels extend from the substrate surface outwards in the direction of the longitudinal axis of the elongated structure. In one embodiment the direction of the channels is essentially perpendicular to the substrate surface where the channels start at the substrate surface. The channels then extend along the longitudinal axis of the elongated structure. When the elongated structures are bent the channels also bend.

In an alternative embodiment the channels extend essentially parallel with the substrate surface. In such an embodiment the elongated structures are on the surface and extending parallel to the surface.

In one embodiment the substrate surface is at least partially hydrophobic. In an alternative embodiment the substrate surface at least partially is treated to become hydrophobic.

In another embodiment the substrate surface is at least partially hydrophilic. In yet alternative embodiment the substrate surface at least partially is treated to become hydrophilic.

In one embodiment the substrate comprises silicon.

In one embodiment the substrate surface is a part of a device selected from the group consisting of a battery, a catalyst, a mesoreactor, a solar cell, and a sensor. In one embodiment the method further comprises the step of utilizing the structures in a process for the manufacture of at least one device selected from the group consisting of a battery, a catalyst, a mesoreactor, a solar cell, and a sensor.

In one embodiment the substrate surface is a part of a drug carrier. In one embodiment the method further comprises the step of utilizing the structures in a process for the manufacture of a drug carrier.

In one embodiment the structures are used during a phase of the manufacturing process and are then removed. An example of removal includes but is not limited to removal by etching. In embodiments where the structures are removed the structures are not present in the final product, but have been used to obtain a desired structure.

In a second aspect there is provided a method for the manufacture of the above described structures on a surface, said method comprising the steps of:

providing a reaction solution, said reaction solution comprising a silicate, a micelle forming agent, an alkane, a salt, and at least 1.5 M HCl, said reaction solution having a pH of 2 or lower, stirring not more than 10 minutes, bringing the reaction solution into contact with a substrate surface treating the obtained material to remove said micelle forming agent with one method selected from a) heat treating the material above 300° C., b) treating the material with at least one selected from $H_2O_2$, and $H_2SO_4$, c) treating the material with microwaves to digest the micelle forming agent.

In one embodiment the method further comprises an initial step wherein the substrate surface is treated to become hydrophobic.

In one embodiment the method further comprises an initial step wherein the substrate surface is treated to become hydrophobic.

In an alternative embodiment the pH is 1.5 or lower. In another embodiment the pH is 1 or lower.

In one embodiment the reaction solution comprises HCl in concentration above 1.4 M. In an alternative embodiment the reaction solution comprises HCl in concentration from 1.4 to 2.5 M. In an alternative embodiment the reaction solution comprises HCl in concentration of at least 2.0 M. In one embodiment the reaction solution comprises HCl in concentration above 1.4 M. In one embodiment the reaction solution comprises HCl in concentration above 1.5 M. In one embodiment the reaction solution comprises HCl in concentration above 1.6 M. In another embodiment the reaction solution comprises HCl in concentration above 1.7 M. In another embodiment the reaction solution comprises HCl in concentration above 1.63 M. In one embodiment the reaction solution comprises HCl in concentration from 1.6 to 2.0 M. In one embodiment the reaction solution comprises HCl in concentration from 1.7 to 2.0 M. In one embodiment the reaction solution comprises HCl in a concentration below 2.5 M. In one embodiment the reaction solution comprises HCl in a concentration below 2.0 M.

In one embodiment the stirring is performed not more than 10 minutes. In another embodiment the stirring is performed not more than 5 minutes. In an alternative embodiment the stirring is performed not more than 4 minutes.

In one embodiment the silicate is at least one silicate selected from the group consisting of tetramethyl orthosilicate, tetraethyl orthosilicate, tetrapropyl orthosilicate, tetrabutyl orthosilicate, and sodium silicate. In an alternative embodiment the silicate is at least one silicate selected from the group consisting of tetraethyl orthosilicate, tetrapropyl orthosilicate, tetrabutyl orthosilicate, and sodium silicate. In one embodiment the silicate is tetraethyl orthosilicate. In one embodiment one silicate selected from the above silicates is used. In an alternative embodiment a mixture of more than one silicate is used.

In one embodiment the micelle forming agent is a triblock copolymer. In one embodiment the micelle forming agent is an ethylene oxide/propylene oxide/ethylene oxide (EP PO EO) triblock copolymer. In one embodiment the micelle forming agent is an $EO_{20}PO_{70}EO_{20}$ triblock copolymer.

In one embodiment the alkane is at least one selected from the group consisting of pentane, hexane, heptane, octane, nonane, decane, undecane, and dodecane. In one embodiment the alkane is heptane.

In one embodiment the salt is at least one selected from the group consisting of $NH_4F$, KCl, and $NaSO_4$. In one embodiment the salt is $NH_4F$.

In one embodiment the time of contact between the reaction solution and the substrate surface is 1 minute to 3 hours. In an alternative embodiment the static conditions under which the reaction solution was in contact with the substrate surface is from 20 minutes to 3 hours.

In one embodiment a hydrothermal treatment of the obtained material is performed after the synthesis. In one embodiment the hydrothermal treatment is performed for a period of from 0 hour to 120 hours. In one embodiment the hydrothermal treatment is performed for a period of time not exceeding 120 hours. In one embodiment the hydrothermal treatment is performed at a temperature from 20° C. to 130° C. In an alternative embodiment the hydrothermal treatment is performed at a temperature from 80° C. to 130° C. Treatment times exceeding 120 hours at 130° C. may result in disintegration of the structures.

In one embodiment the structures are dried at elevated temperature prior to use. In one embodiment the temperature is above 100° C., in an alternative embodiment the temperature is 200° C. or higher.

Examples

Figure 2:
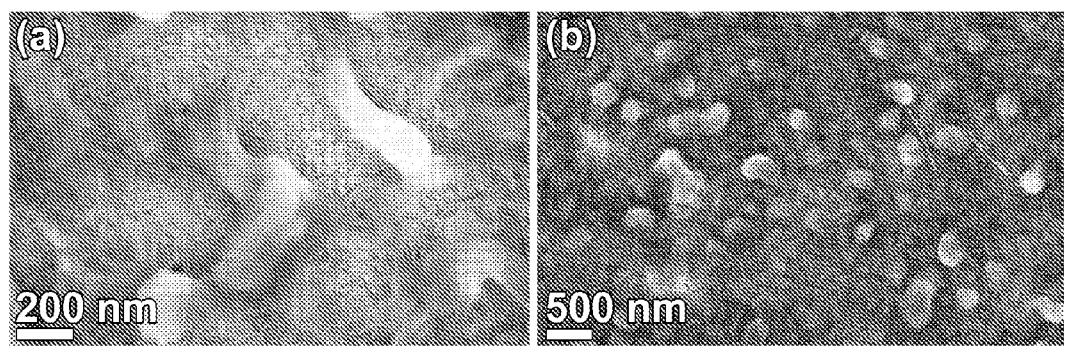
FIG. 2 shows scanning electron micrographs of the structure synthesized with 17 ml of heptane on a (a) hydrophobic and (b) hydrophilic substrate.

In a typical synthesis 2.4 g of P123 and 0.028 g of $NH_4F$ was dissolved in 80 ml 1.83 M HCl solution. The mixture was stirred at 20° C. until the polymer was dissolved. 17 ml heptane was premixed with 5.5 ml TEOS and then added to the micellar solution. The synthesis was kept under vigorous stirring for 4 min and then under static conditions for 1 h. During the static time silicon wafers treated to be hydrophobic were immersed into the synthesis. The substrates were added to the synthesis solution after the start of the static time. After the reaction the solution and substrates were transferred to an autoclave for hydrothermal treatment at 100° C. for 24 h. The resulting film can be seen in FIG. 1 and FIG. 2(a).

In another synthesis, hydrophilic substrates and 17 ml heptane was used. The substrates were immersed into the synthesis 45 s after the start of the static time. The film can be seen in FIG. 2(b).

Figure 3:
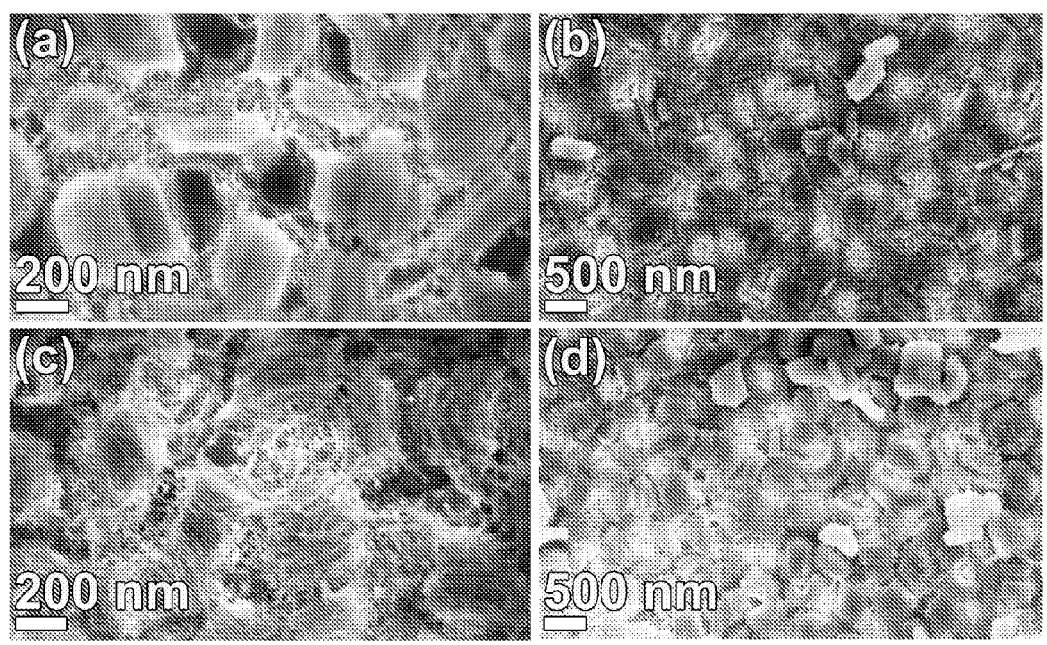
FIG. 3 shows scanning electron micrographs of the structure synthesized with 1 ml of heptane on a (a) and (b) hydrophobic and (c) and (d) hydrophilic substrate.
Figure 4:
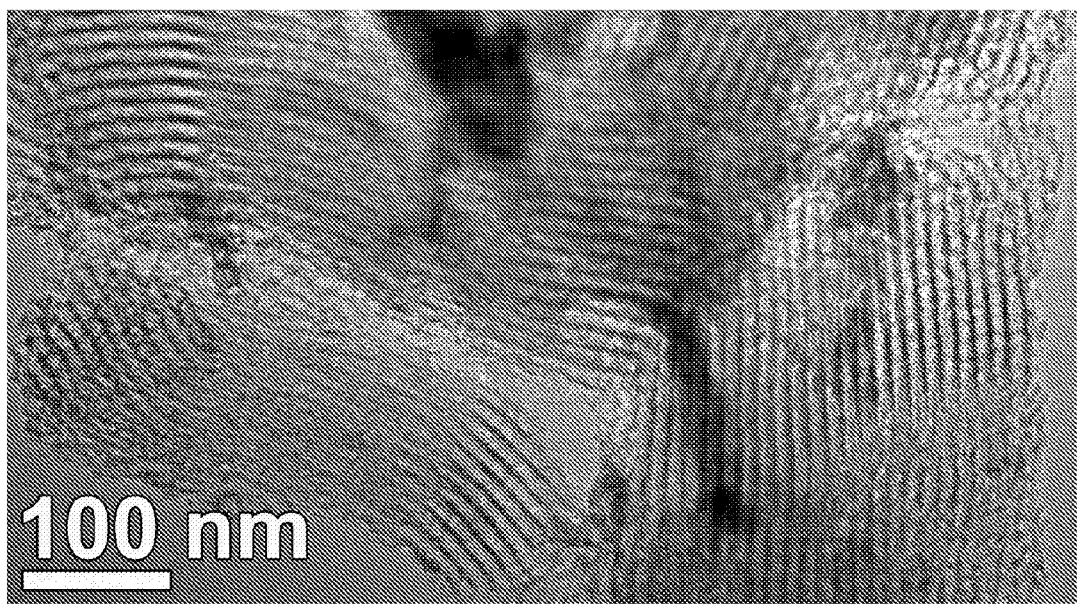
FIG. 4 shows a transmission electron micrograph of the structure synthesized with 1 ml heptane on a hydrophobic substrate.
Figure 5:
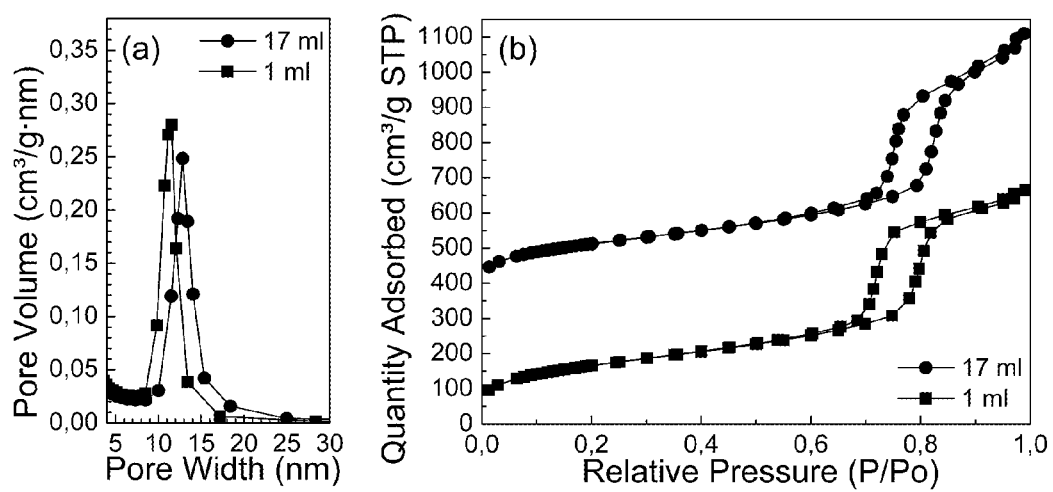
FIG. 5 shows (a) the pore size distributions and (b) physisorption isotherms from nitrogen adsorption measurements of the particles attached on the surfaces when different amounts of heptane are used.

In another synthesis, the amount of heptane was decreased from 17 ml to 1 ml. The hydrophobic and hydrophilic substrate was immersed to the solution after a static time of 30 s. The resulting films are seen in FIG. 3 and FIG. 4. The pore size distributions and physisorption isotherms for films synthesized with 17 ml or 1 ml heptane are seen in FIG. 5.

In another synthesis, 1 ml heptane was used and substrates were immersed into the solution 20-180 s into the static time.

Figure 6:
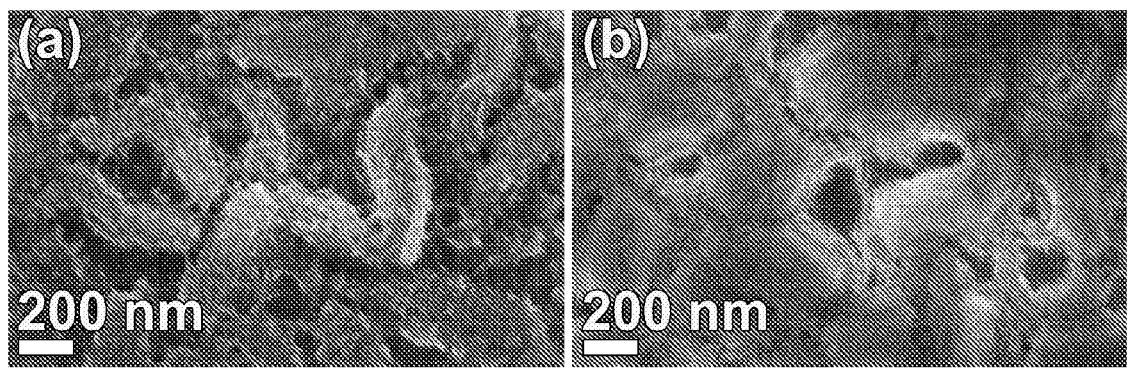
FIG. 6 shows scanning electron micrographs of the structure formed on a substrate after (a) 5 min and (b) 180 min.

In another synthesis, the hydrophobic substrates were added to the solution after 30 s into the static and redrawn from the synthesis after 5-180 min. In this synthesis 1 ml heptane was used. Examples of these films are seen in FIG. 6.

Figure 7:
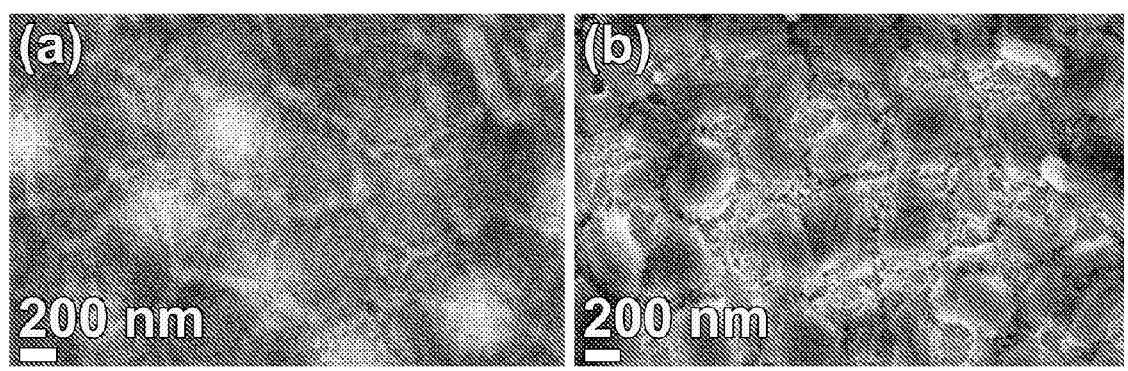
FIG. 7 shows scanning electron micrographs of the structure synthesized with a hydrothermal treatment time of (a) 0.5 h and (b) 48 h.

In other syntheses, the hydrothermal treatment time was varied between 0-48 h. The substrates were hydrophobic and 1 ml heptane was used in the synthesis. Examples of these films are seen in FIG. 7.

To vary the surface hydrophilicity of the silicon wafers, they were first cleaned with TL1 wash ($H_2O$, $H_2O_2$ and $NH_3$) followed by treatment in $HNO_3$ in ambient temperature for 5 min. This increases the number of OH groups and thereby the hydrophilicity of the silicon wafer surface. To get hydrophobic substrates the wafers were then treated with octadecytrichlorosilane in a heptane solution for 10 min. Prior to the use of the substrates they were dried in an oven at 200° C. for 1 h.

The invention claimed is:

1. A method for the manufacture of structures on a substrate surface, said method comprising the steps of:
    (a) providing a reaction solution, said reaction solution comprising a silicate, a micelle forming agent, an alkane, a salt, and at least 1.4 M HCl, said reaction solution having a pH of 2 or lower;
    (b) stirring the reaction solution in step (a) for not more than 5 minutes, and wherein the stirring is performed at a temperature of 20° C.;
    (c) bringing the reaction solution from step (b) into contact with said substrate surface during which time the structures are manufactured on the substrate surface; and
    (d) treating material obtained in step (c) to remove said micelle forming agent with a method selected from the group consisting of heat treating the material above 300° C., treating the material with at least one compound selected from the group consisting of $H_2O_2$ and $H_2SO_4$, and treating the material with microwaves to digest the micelle forming agent;
    wherein the manufactured structures on said substrate surface at least partially comprise at least one elongated structure, wherein each of the elongated structures comprises a plurality of channels, said channels extending in the direction of the longitudinal axis of the elongated structure, wherein said channels extend from the substrate surface outwards in the direction of the longitudinal axis of the elongated structure, and wherein said at least one elongated structure comprises silicon dioxide.

2. The method according to claim 1, wherein the method further comprises treating the substrate surface to become hydrophobic or hydrophilic before the reaction solution is brought into contact with the substrate surface in step (c).

3. The method according to claim 1, wherein the silicate is at least one silicate selected from the group consisting of tetramethyl orthosilicate, tetraethyl orthosilicate, tetrapropyl orthosilicate, tetrabutyl orthosilicate, and sodium silicate.

4. The method according to claim 1, wherein the micelle forming agent is a triblock copolymer.

5. The method according to claim 1, wherein the alkane is at least one alkane selected from the group consisting of pentane, hexane, heptane, octane, nonane, decane, undecane, and dodecane.

6. The method according to claim 1, wherein the salt is at least one salt selected from the group consisting of $NH_4F$, KCl, and $NaSO_4$.

7. The method according to claim 1, further comprising hydrothermally treating the material obtained in step (c).

8. The method according to claim 7, wherein said hydrothermal treatment step is performed at a temperature from 20° C. to 130° C.

* * * * *